(12) United States Patent
Kanefsky et al.

(10) Patent No.: US 11,106,869 B1
(45) Date of Patent: Aug. 31, 2021

(54) FACILITATING PHARMACY CUSTOMER ORDERS THROUGH NATURAL LANGUAGE PROCESSING

(71) Applicant: WALGREEN CO., Deerfield, IL (US)

(72) Inventors: Lindsey Kanefsky, Chicago, IL (US); Kartik Subramanian, Chicago, IL (US); Andrew Schweinfurth, Chicago, IL (US); Benjamin Weiss, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 120 days.

(21) Appl. No.: 16/110,216

(22) Filed: Aug. 23, 2018

(51) Int. Cl.
*G06F 16/835* (2019.01)
*G06F 40/30* (2020.01)
*H04W 4/14* (2009.01)
*G16H 20/10* (2018.01)
*G06N 20/00* (2019.01)

(52) U.S. Cl.
CPC .............. *G06F 40/30* (2020.01); *G06N 20/00* (2019.01); *G16H 20/10* (2018.01); *H04W 4/14* (2013.01)

(58) Field of Classification Search
CPC ............................... H04L 51/32; G06F 16/835
See application file for complete search history.

(56) References Cited

U.S. PATENT DOCUMENTS

| | | | | |
|---|---|---|---|---|
| 8,433,587 | B1* | 4/2013 | Cullen | G06F 19/3456 705/3 |
| 2008/0147514 | A1* | 6/2008 | Shuster | G06Q 30/0603 705/26.8 |
| 2011/0082705 | A1* | 4/2011 | Kobylevsky | G06Q 10/10 705/2 |
| 2018/0013699 | A1* | 1/2018 | Sapoznik | G06F 40/205 |
| 2018/0084394 | A1* | 3/2018 | Demele | B60Q 9/00 |
| 2018/0365702 | A1* | 12/2018 | Sehrawat | H04L 51/32 |
| 2019/0087455 | A1* | 3/2019 | He | G06F 40/253 |
| 2019/0171711 | A1* | 6/2019 | Carpenter, II | G10L 13/02 |
| 2019/0182383 | A1* | 6/2019 | Shaev | H04M 3/527 |

* cited by examiner

*Primary Examiner* — Daniel Abebe
(74) *Attorney, Agent, or Firm* — Marshall, Gerstein & Borun LLP; Randall G. Rueth (57) ABSTRACT

A computer-implemented method includes receiving a message of a pharmacy customer wherein the message includes a text string, and generating a set of one or more intents corresponding to the pharmacy customer by analyzing the text string using a trained machine learning model, wherein each of the one or more intents correspond to a respective desired action pertaining to the pharmacy order. The machine learning model may be a classification model. The method further includes generating at least one response message based on the set of intents corresponding to the pharmacy customer and transmitting the at least one response message to a mobile device associated with the pharmacy customer. The set of one or more intents may be chosen from a list of commonplace pharmacy customer intents.

20 Claims, 7 Drawing Sheets

```
In [97]: classify("Hell yes please refill")
Out [97]: ('RefillRequest', 0.6166666666666667)
In [98]: classify("Already picked")
Out [98]: ('AlreadyPickedUp', 0.12083333333333333)
In [99]: classify("who is this")
Out [99]: ('UnknownIntent', 0.09741784037558684)
In [100]: classify("I'm driving - Sent from my car")
Out [100]: ('DrivingInCar', 2.5909090909090904)
```

In [28]: `test_data = ["Hell yes please refill", "Already picked", "who is this", "I'm driving - Sent from my car"]`

In [29]: `test_labels = ["RefillReqeust", "AlreadyPickedUp", "UnknownIntent", "DrivingInCar"]`

In [30]:
```
# Representation of the data using TF-IDF
vectorizer = TfidfVectorizer()
vectorised_train_data = vectorizer.fit_transform(train_data)
vectorised_test_data = vectorizer.transform(test_data)

# Train the classifier given the training data
classifier = LinearSVC()
classifier.fit(vectorised_train_data, train_labels)
```

Out [30]: `LinearSVC(C=1.0, class_weight=None, dual=True, fit_intercept=True,
          intercept_scaling=1, loss='squared_hinge', max_iter=1000,
          multi_class='ovr', penalty='l2', random_state=None, tol=0.0001,
          verbose=0)`

In [31]:
```
# Predict the labels for the test documents (not used for training)
print(classifier.predict(vectorised_test_data))
```

`['RefillRequest' 'AlreadyPickedUp' 'WrongNumber' 'DrivingInCar']`

In [29]:
```
x = np.array(training)
y = np.array(output)

start_time = time.time()

train(X, y, hidden_neurons=20, alpha=0.1, epochs=100000, dropout=False, dropout_percent=0.2)

elapsed_time = time.time() - start_time
print ("processing time:", elapsed_time, "seconds")
```

342

```
Training with 20 neurons, alpha:0.1, dropout:False
Input Matrix: 398x478    Output matrix: 1x12
delta after 10000 iterations:0.0269139014267
delta after 20000 iterations:0.0112263487938
delta after 30000 iterations:0.0107287977719
delta after 40000 iterations:0.0104505918798
delta after 50000 iterations:0.0104044186401
delta after 60000 iterations:0.0103773703023
delta after 70000 iterations:0.0103587729022
delta after 80000 iterations:0.0103448116321
delta after 90000 iterations:0.0103338866465
delta after 100000 iterations:0.0103250060769
saved synapses to: synapses.json
processing time: 190.837211132049956 seconds
```

FIG. 3C

```
classify("Hell yes please refill")
classify("Already Picked")
classify("who is this")
classify("I'm Driving - Send from my car")
print()
classify("picked", show_details=True)

Hell yes please refill
   classification:  []
Already Picked
   classification:  [['AlreadyPickedUp', 0.9971848808675334]]
who is this
   classification:  [['UnknownIntent', 0.9940201653882535]]
Sent from my car
   classification:  []

found in bag: pick
SMS: picked
```

FACILITATING PHARMACY CUSTOMER ORDERS THROUGH NATURAL LANGUAGE PROCESSING

FIELD OF THE DISCLOSURE

The present disclosure generally relates to a system and method for facilitating pharmacy customer orders through natural language processing of text messages (e.g., short message service (SMS) messages).

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

From the perspective of a pharmacy patient/customer, the routine and conventional method of placing and/or refilling prescription orders includes interacting with a brick-and-mortar pharmacy by visiting the pharmacy in person and/or by telephoning the pharmacy. From the perspective of a pharmacy and/or pharmacist, the conventional and routine methods of placing and/or refilling the prescription order may include serving the needs of a pharmacy patient/customer by responding to discussions via telephone and/or in person. In the routine and conventional pharmacist/patient relationship, information (e.g., patient information, pharmacy information, prescription information, etc.) may be exchanged between the pharmacist/pharmacy and the customer/patient. However, pharmacies currently lack robust methods and systems for automatically receiving and dispatching messages sent from the customer/patient to the pharmacist/pharmacy.

While routine and conventional pharmacist/patient interaction may include a ref ill-by-text service, that service may be limited to only keyword-based messaging, and may not be able to understand any contextual information, or messages sent in an imprecise format. In some cases, a customer may be able to send a text message to a pharmacy to express an intent of the customer. For example, the customer may require a prescription refill. An existing method and system of a pharmacy may be able to receive a message from a customer (e.g., a text message) and to identify keywords in the message (e.g., "refill" or "status") indicating the customer's intent. However, existing methods and systems suffer from drawbacks which severely limit their use.

For example, existing methods and systems can only determine customer intent if the message contains a specific, pre-determined keyword, and are unable to handle messages which express a customer's intent using language which has not been pre-programmed. However, currently, it is common for customers to send written messages that are not supported by these existing methods and systems. Many customers send pharmacy-related text messages, or non-pharmacy-related text messages (e.g., messages wherein the pharmacy is an unintended recipient), that are not understood, and the pharmacy may not respond appropriately. This lack of support and improper responses may cause customer confusion and/or frustration. Further, existing systems lack any mechanism for delaying or deferring messages to customers, even if the customer is unavailable (e.g., driving a car).

More generally, a pharmacy customer may benefit greatly from pharmacy methods and systems that do not require the pharmacy customer to transact business in person. Pharmacies may also benefit due to more efficient handling of pharmacy customer orders.

BRIEF SUMMARY

This Brief Summary is provided to introduce a selection of concepts that are further described below in the Detailed Description in a simplified form. This Brief Summary is not intended to identify key features or essential features of the claimed subject matter, nor is it intended to be used to limit the scope of the claimed subject matter.

In one aspect, a computer-implemented method of facilitating a pharmacy order includes receiving, in an application server, a message of a pharmacy customer. The message includes a text string. The method also includes generating a set of one or more intents of the pharmacy customer by analyzing the text string using a trained machine learning model. Each of the one or more intents corresponds to a respective desired action pertaining to the pharmacy order. The method also includes generating, based on the set of intents corresponding to the pharmacy customer, at least one response message, and transmitting the at least one response message to a mobile device associated with the pharmacy customer.

In another aspect, a computing system includes one or more processors and memory storing instructions that, when executed by the one or more processors, cause the computing system to receive, in an application server, a message of a pharmacy customer. The message includes a text string. The instructions further cause the computing system to select, from a set of one or more trained machine learning models, a trained machine learning model, and generate, by analyzing the text string using the trained machine learning model, a set of one or more intents of the pharmacy customer. Each of the one or more intents corresponds to a respective desired action pertaining to the pharmacy order. The instructions also cause the computing system to generate, based on the set of intents corresponding to the pharmacy customer, at least one response message, transmit the at least one response message to a mobile device associated with the pharmacy customer, and cause the at least one response message to be displayed in a display device of the mobile device.

In another aspect, a computing system includes a mobile device configured to execute an application that causes an inbound message to be transmitted via a carrier network. The computing system also includes a server device configured to execute an application that causes the inbound message to be received via the carrier network. The server device is configured to, after receiving the inbound message via the carrier network, analyze the inbound message using a trained machine learning model, and identify a customer intent corresponding to the inbound message. The server device is also configured to perform an action based on the customer intent with respect to a pharmacy order corresponding to the customer, to generate an outbound text message addressed to the mobile device, and to transmit the outbound text message to the mobile device via the carrier network.

DETAILED DESCRIPTION

Although the following text sets forth a detailed description of numerous different embodiments, it should be understood that the legal scope of the description is defined by the words of the claims set forth at the end of this text. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term" "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

The system and method of facilitating a pharmacy order described herein provide a pharmacy with the ability to understand the utterances and/or messages of pharmacy customers who are remote from the pharmacy, and to take action in response to that understanding. The system and method may provide a pharmacy with a fully automated way to determine pharmacy customer intent with respect to pharmacy business, and to dispatch pharmacy customer requests to appropriate pharmacy staff based on the customer's intent. The method and system may further allow a pharmacy to determine pharmacy customer intent based on a general understanding of a message from the pharmacy customer, without resorting to keyword matching. As such, it is no longer necessary for the pharmacy to identify or enumerate every possible permutation of a message that a pharmacy customer may conceivably send to the pharmacy in advance of receiving such a message.

Example Customer Order Facilitation System

Figure 1:
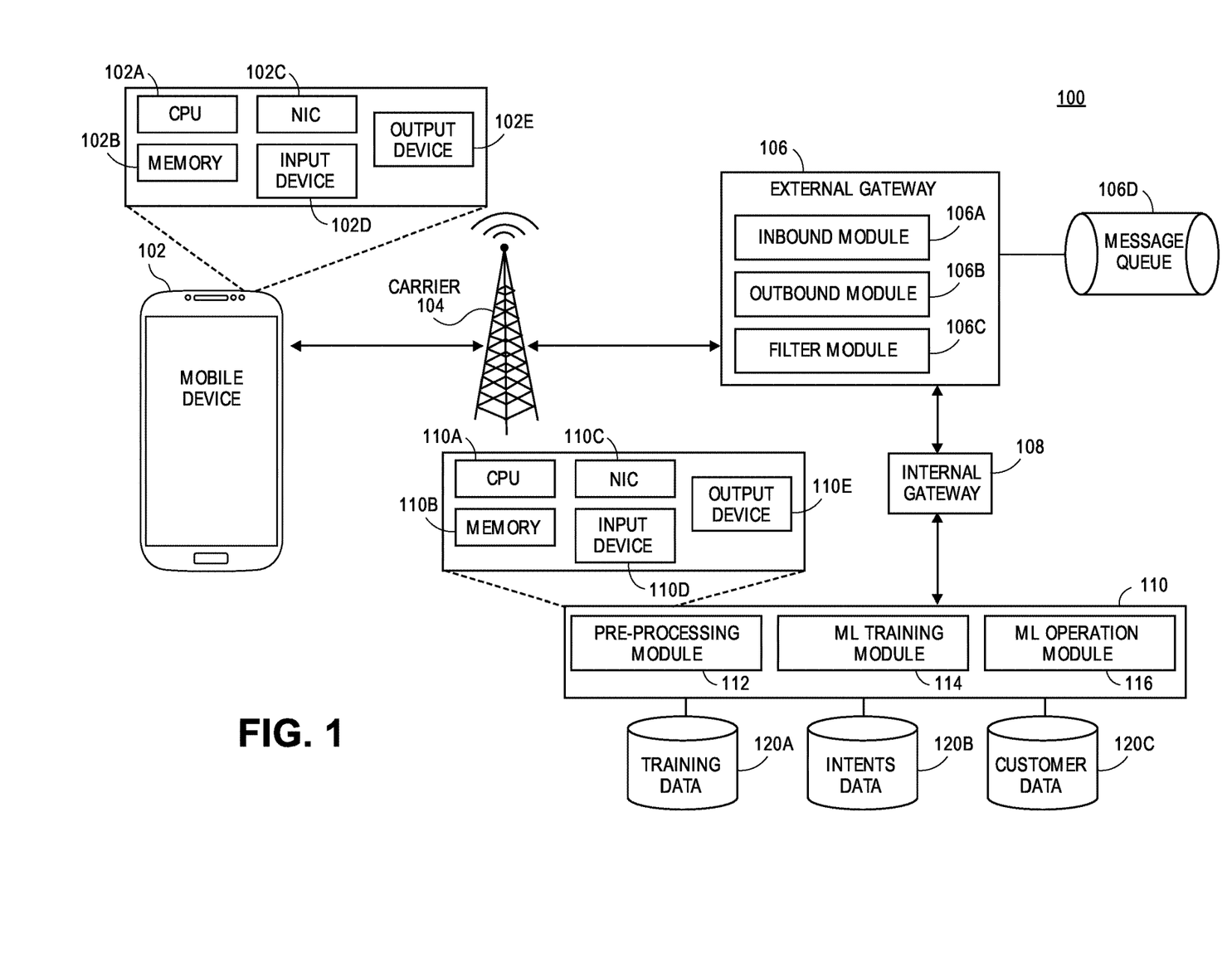
FIG. 1 is an example block diagram of a system for facilitating a pharmacy customer order.

FIG. 1 depicts various aspects of an example system 100 for facilitating a pharmacy customer order. The high-level architecture of system 100 includes both hardware and software components, as well as various channels for communicating data between the hardware and software components. The system 100 may include hardware and software modules that employ methods of determining customer intent for purposes of facilitating pharmacy customer orders (e.g., prescription refill orders). The modules may be implemented as computer-readable storage memories containing computer readable instructions (i.e., software) for execution by a processor of the system 100.

The system 100 may include a mobile device 102, which may communicate via a carrier network 104 to other components of system 100. The mobile device 102 may allow a user of the mobile device 102 (e.g., a pharmacy customer) to send and receive messages. As used herein, a "message" may include any sort of electronic message that comprises or is composed of textual or text-like data, such as a text/SMS message, an email, a voice mail, an audio recording, a tweet, etc. Moreover, a "message" may be expressed in any text encoding(s), and may include whitespace and/or non-printing characters. In some embodiments, wherein the message is a voice recording, the message may be referred to as an "utterance," meaning one or more words/phrases spoken by the customer. An utterance may be converted to a text message and processed according to the principles disclosed herein.

The mobile device 102 may include a personal computer, smart phone, laptop, tablet, or other suitable computing device. The mobile device 102 may include various hardware components, such as a central processing unit (CPU) 102A, a memory 102B, a network interface controller (NIC) 102C, an input device 102D, and/or an output device 102E. The CPU 102A may include any number of processors, possibly including one or more graphics processing unit (GPU). The memory 102B may include a random-access memory (RAM), a read-only memory (ROM), a hard disk drive (HDD), a magnetic storage, a flash memory, a solid-state drive (SSD), and/or one or more other suitable types of volatile or non-volatile memory. The NIC 102C may include one or more physical networking devices (e.g., an Ethernet device, a wireless network controller, etc.). The NIC 102C may allow the mobile device 102 to communicate with other components of the system 100 via a computer network such as the carrier network 104. The input device 102D may include one or more peripheral device such as a detached keyboard or mouse, or an integral device such as a capacitive touch screen of a portable computing device. The input device 102D may include a microphone, in some embodiments. The output device 102E may be a suitable display device such as a computer monitor, capacitive touch screen, television screen, etc.

As noted, in some embodiments, the mobile device 102 may connect to other components via a computer network such as the carrier network 104. Although the carrier network 104 may be a wireless network of a consumer network provider (e.g., a Global System for Mobile communication (GSM) provider or Code Division Multiple Access (CDMA) provider), in some embodiments the carrier network 104 may be a private wireless network. Mobile device 102 may send messages to the carrier network 104 via SMS short codes. In some embodiments, the carrier network 104 may include an Internet Service Provider (ISP) such as a Tier 1 and/or Tier 2 network. In some embodiments, the carrier network 104 may include the Internet and/or another suitable network (e.g., a local area network (LAN), a metropolitan area network (MAN), a wide area network (WAN), a mobile, a wired or wireless network, a virtual private network (VPN), etc.). As noted, the mobile device 102 may connect to other components of system 100 via carrier network 104.

The other components of system 100 may include an external gateway 106, an internal gateway 108, and a server 110. The external gateway 106 may be a message gateway that is outside a physical network and/or a logical network of the proprietor of the server 110 (e.g., a pharmacy). For example, the external gateway 106 may be or include an SMS application programming interface (API) service provided by a third party. The internal gateway 108 may be a message gateway that is located inside the logical network and/or physical network of the proprietor of the server 110 (e.g., the internal gateway 108 may be located in a data center owned/controlled by the pharmacy). In this way, the external gateway 106 and the internal gateway 108 may be segregated for purposes of network infrastructure.

The external gateway 106 and the internal gateway 108 may be implemented as one or more hardware devices. For example, the external gateway 106 and the internal gateway 108 may both be implemented in a single hardware device, as separate modules. Alternatively, the external gateway 106 and the internal gateway 108 may be implemented in a router and/or a switch. In an embodiment, internal gateway 108 may be implemented within the server 110.

The external gateway 106 may include an inbound module 106A, an outbound module 1066, a filter module 106C, and a message queue 106D. Generally, the inbound module 106A may include instructions for receiving carrier messages from carrier network 104, and for sending carrier messages to the internal gateway 108. Generally, the outbound module 1066 may include instructions for receiving messages from the internal gateway 108 and for sending messages to systems or devices (e.g., mobile device 102) via the carrier network 104. Sending and receiving carrier messages may be performed by the external gateway 106 using a carrier API, which may differ depending on the carrier associated with carrier network 104. For example, a different carrier API may be chosen, depending on whether the mobile device 102 is associated with a CDMA carrier or a GSM carrier. The inbound module 106A may include instructions for unpacking carrier messages to decode message payloads, and the outbound module 1066 may include instructions for encoding message payloads into carrier messages. The inbound module 106A may also include instructions for filtering messages through the filter module 106C. For example, the filter module 106C may include instructions for coarse filtering, wherein only a small subset of messages is captured, and the remainder are discarded. Both inbound messages (i.e., messages bound for the carrier network 104 originating from the mobile device 102) and outbound messages (i.e., messages bound for the carrier network 104 originating from the server 110) may include message metadata. For example, a telephone number, a sequence number, etc. may be associated with each message and included in the message metadata of that message.

The filter module 106C may be configured to allow only those messages meeting certain criteria to pass from the carrier network 104 to the input module 106A, and/or from the input module 106A to the internal gateway 108. For example, in an embodiment, the filter module 106C may include or have access to a list of keywords (e.g., as stored in a database of external gateway 106, not shown in FIG. 1). Any message not including at least one of the keywords in the list of keywords may be discarded or deferred (e.g., moved to the message queue 106D or an electronic database).

The message queue 106D may receive inbound messages filtered by filter module 106C that match a keyword (e.g., as filtered by a coarse filter). The message queue 106D may also receive outbound messages. For example, the message queue 106D may receive all inbound and/or outbound messages in the event that the memory of the external gateway 106 and/or the internal gateway 108 fills up or reaches a predetermined limit. The message queue 106D may be implemented as any suitable message queue (e.g., as a UNIX message queue, as an Advanced Message Queuing Protocol (AQMP) message queue, as a relational database, etc.). The external gateway 106 and internal gateway 108 may retrieve messages from, and write messages to, the message queue 106D.

The internal gateway 108 may be an interface for receiving inbound messages from the mobile device 102 via the carrier network 104 and the external gateway 106, and may also be an interface for sending messages to the external gateway 106 from the server 110.

The server 110 may be a backend component of the system 100. The server 110 may include various hardware components, such as a CPU 110A, a memory 110B, a NIC 110C, an input device 110D, and/or an output device 110E. The CPU 110A may include any number of processors, possibly including one or more GPUs. The memory 110B may include a RAM, a ROM, a HDD, a magnetic storage, a flash memory, an SSD, and/or one or more other suitable types of volatile or non-volatile memory. The NIC 110C may include one or more physical networking devices (e.g., an Ethernet device, a wireless network controller, etc.). The NIC 110C may allow the server 110 to communicate with other components of the system 100 via a computer network such as the carrier network 104. The input device 110D may include one or more peripheral device such as a detached keyboard or mouse, or an integral device such as a capacitive touch screen of a portable computing device. The output device 110E may be a suitable display device such as a computer monitor, capacitive touch screen, television screen, etc. In some embodiments, the server 110 may be located at the premises of a retail pharmacy or a facility related to a retail pharmacy (e.g., a corporate office, data-center, etc.). In those embodiments, a pharmacist, pharmacy technician, retail pharmacy staff member, or other employee of a pharmacy company may interact with the server 110 via the input device 110D, and/or via a computer terminal communicatively coupled to the server 110D.

The server 110 may include one or more modules implemented as hardware and/or computer readable instructions (e.g., software). For example, the server 110 may include a pre-processing module 112, a machine learning (ML) training module 114, and an ML operation module 116. The pre-processing module 112, the ML training module 114, and the ML operation module 116 may act in concert to retrieve labeled data, to train and/or receive machine learning models, and to use the trained machine learning models to produce valuable outputs, respectively, as discussed further below. The server 110 may include an application server. The application server may be any suitable application server, such as a Java Application Server.

The pre-processing module 112 may be used both during ML training and ML operation, and in general acts to clean and normalize training data and input data so that the data can be uniformly processed by ML training module 114 and/or the ML operation module 116. For example, the pre-processing module 112 may be used to remove emojis, special characters, whitespace, etc.

The ML training module 114 may be programmed to read a training data set, either in raw form or via the pre-processing module 112. The training data set contains a plurality of messages, and each of the plurality of messages is labeled with one intent of a set of intents. The ML training module 114 may use the training data set to train a classifier ML model to predict one intent of the set of intents. Once trained, the ML training module 114 may analyze other, unknown or arbitrary messages and correctly predict an intent associated with those messages. The ML training module 114 may include instructions for saving the trained model to an electronic database, and/or for loading a saved, trained model from an electronic database or via the carrier network 104 or another computer network. The ML training module 114 may include instructions for incrementally training a model (i.e., for "online" training). For example, the ML training module may be trained with an initial batch of training messages representing messages received from pharmacy customers over a period of one year. Then, as new messages are received and labeled, the existing ML model may be trained using the new messages, thereby making the existing ML model more accurate, without the need to retrain on the first batch of training messages.

The ML operation module 116 may load the trained ML model and execute the trained ML model using input data (i.e., apply the input data to the trained ML model). The input data may be test data (e.g., a validation data set used to test the accuracy, precision, and/or recall of the model) or new data from a real-world scenario (e.g., a message texted to the server 110 by a customer). The ML operation module 116 may include instructions for identifying an intent (e.g., a class) output by the trained ML model, and for passing that class to an intent processing module (not shown in FIG. 1). The input and/or training data set may be read from files, such as comma-separated-value (CSV) files. Many such files may be used. For example, one file may be read for each respective date in a window, and/or for each individual pharmacy customer.

The server 110 may be communicatively coupled to one or more electronic databases that store training data 120A, intents data 120B, and customer data 120C. The server 110 may receive messages from the internal gateway 108, and may send messages via the internal gateway 108.

The training data 120A may include labeled data used to train machine learning models, as discussed above. For example, the training data 120 may include a set of messages wherein each message is associated (labeled) with an intent. The intents data 120B may include a set of intents, wherein each intent specifies an objective or desire of a pharmacy customer. The customer data 120C may include a data set of customers, wherein each customer in the set of customers represents a unique pharmacy customer. The customer data 120C may include personal information, such as the customer's date of birth, mailing address, telephone number, etc. The customer data 120C may also include the subscription status of the customer (e.g., whether the customer has signed up to receive prescription refill alerts via text message) and the prescription status of the customer (e.g., any prescriptions that are currently associated with the customer, and the respective status of those prescriptions). For example, in some embodiments, the customer data 120C may include a "last filled" date of a prescription, a "time until refill" timestamp, etc. In some embodiments, a one-to-one, one-to-many, and/or many-to-many relationship may be established between any of the input data, training data 120, the intents data 120B, and/or the customer data 120C. For example, one or more database table may be created which include linkages between messages sent by a pharmacy customer (e.g., a message such as "refill my inhaler") and stored in the customer data 120C, one or more corresponding intents (e.g., RefillRequest) stored in the intents data 120B, and/or data stored in other databases.

In operation, a customer may possess the mobile device 102. The customer may register the mobile device 102 within the server 110 or external gateway 106 by sending a text message (e.g., the text string "SUBSCRIBE") to a predetermined telephone number (e.g., as discussed above, an SMS short code). In some embodiments, the customer may register the mobile device 102 via other means, such as via a web site, via a mobile application, via telephone, and/or in person. During the subscription process, the mobile device 102 may be associated with the customer via a patient ID, which may be used in the server 100 to identify the customer.

Once the mobile device 102 of the customer is registered, a message sent by the customer may be routed from the mobile device 102 via the carrier network 104 to the inbound module 106A. The inbound module 106A may pass the message to the internal gateway 108, and the internal gateway 108A may pass the message to the pre-processing module 112. The pre-processing module 112 may clean the message by removing extraneous information, and may then pass the message to the ML operation module 116.

By the time the ML operation module 116 receives the cleaned message, the ML training module 114 may have trained one or more ML models. Therefore, the ML operation module 116 may select an appropriate trained model at the time the ML operation module 116 receives the cleaned message. The ML operation module 116 may select a trained model by any suitable means. For example, the ML operation module 116 may analyze the area code of the message metadata associated with the cleaned message and, based on the area code, may select a particular trained model. In another embodiment, the system 100 may include instructions for analyzing the telephone number associated with the cleaned message to identify a customer, and for retrieving one or more ML models associated with that customer or an attribute of that customer (e.g., whether the customer is a known customer of the pharmacy or a new customer of the pharmacy).

The ML operation module 116 may initialize the trained model by, for example, setting the initial parameters or hyperparameters of the trained model. Model parameters may be stored in an electronic database accessible by server 110, such as training data 120A. The ML operation module 116 may then apply the cleaned message to the trained, initialized ML model. The trained ML model may output an intent associated with the cleaned message of the customer, and based on the intent, additional actions may be taken by the system 100, or another system (e.g., as discussed further below).

In general, training ML models may include establishing a network architecture, or topology, and adding layers that may be associated with one or more activation functions (e.g., a rectified linear unit, softmax, etc.), loss functions and/or optimization functions. Multiple different types of artificial neural networks may be employed, including without limitation, recurrent neural networks, convolutional neural networks, and/or deep learning neural networks. Data sets used to train the artificial neural network(s) may be divided into training, validation, and testing subsets, and these subsets may be encoded in an N-dimensional tensor, array, matrix, or other suitable data structures. Training may be performed by iteratively training the network using labeled training samples. Training of the artificial neural network may produce byproduct weights, or parameters which may be initialized to random values. The weights may be modified as the network is iteratively trained, by using one of several gradient descent algorithms, to reduce loss and to cause the values output by the network to converge to expected, or "learned", values. In an embodiment, a regression neural network may be selected which lacks an activation function, wherein input data may be normalized by mean centering, to determine loss and quantify the accuracy of outputs. Such normalization may use a mean squared error loss function and mean absolute error. The artificial neural network model may be validated and cross-validated using standard techniques such as hold-out, K-fold, etc. In some embodiments, multiple artificial neural networks may be separately trained and operated, and/or separately trained and operated in conjunction. In another embodiment, a Bayesian model may be used to train the ML model.

In an embodiment, the ML model may include an artificial neural network having an input layer, one or more hidden layers, and an output layer. Each of the layers in the artificial neural network may include an arbitrary number of neurons. The plurality of layers may chain neurons together linearly and may pass output from one neuron to the next, or may be networked together such that the neurons communicate input and output in a non-linear way. In general, it should be understood that many configurations and/or connections of artificial neural networks are possible. In an embodiment, the input layer may correspond to input parameters that are given as full sentences, or that are separated according to word or character (e.g., fixed width) limits. The input layer may correspond to a large number of input parameters (e.g., one million inputs), in some embodiments, and may be analyzed serially or in parallel. Further, various neurons and/or neuron connections within the artificial neural network may be initialized with any number of weights and/or other training parameters. Each of the neurons in the hidden layers may analyze one or more of the input parameters from the input layer, and/or one or more outputs from a previous one or more of the hidden layers, to generate a decision or other output. The output layer may include one or more outputs, each indicating a predicted intent. In some embodiments and/or scenarios, the output layer includes only a single output/intent.

Example Machine Learning Model Training and Operation

Figure 2:
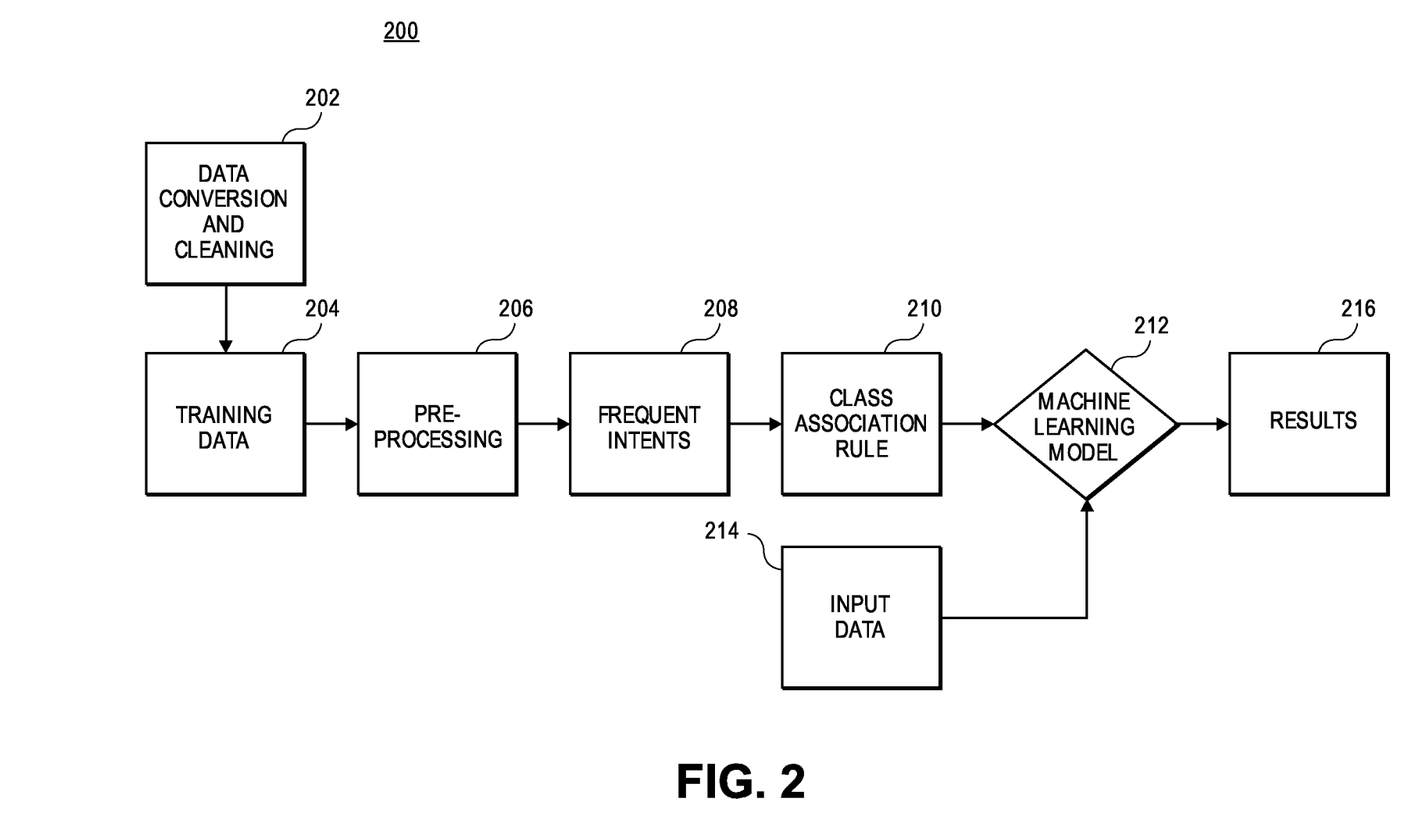
FIG. 2 is an example data flow diagram for training and/or operating a machine learning model to facilitate a pharmacy customer order.

FIG. 2 is a data flow diagram 200 illustrating the training and/or operation of a machine learning model to facilitate a pharmacy customer order, according to one embodiment. The data flow diagram 200 includes a data conversion and cleaning process 202, training data 204, and pre-processing process 206. As discussed below, customers may send messages to the pharmacy that do not evince any discernible intent (e.g., even a human reviewer may not be able to label the message with an intended pharmacy action). These messages may be stored in the training data 204. In one embodiment, the data conversion and cleaning process 202 may label such indiscernible messages accordingly (e.g., by labeling such messages as Unknown Intent messages), or may prune messages from the training data 204. That is, one goal of the data conversion and cleaning process 202 may be to remove messages that are not pertinent to training a relevant intent. For example, a message stating "Hello, Jill." may not evidence any relevant customer intent, and may be removed during the execution of the data conversion and cleaning process 202 and/or flagged as irrelevant.

The pre-processing module 112 of FIG. 1 may perform some or all of data conversion and cleaning process 202 and may perform other operations such as converting all of the text encodings in the training data 204 to a common character encoding (e.g., UTF-8), and/or converting flat/linear data structures (e.g., CSV) into hierarchical data structures (e.g., XML).

After the training data 204 has been converted and cleaned, the pre-processing process 206 may pre-process the training data 204. As discussed above, training data 204 may include data read from CSV files, and may be in a key/value format, wherein the keys are the messages and the values are the respective labels. The pre-processing process 206 may include more in-depth text processing of the training data 204, such as the removal of emojis, case normalization, spelling correction, grammar correction, language translation(s), word stemming, the removal of duplicate messages, etc. In some embodiments, the pre-processing module 112 of FIG. 1 may perform the pre-processing process 206. Although pre-processing may be a useful step, in some embodiments and/or scenarios, no pre-processing is done After pre-processing the pre-processed data, a set of frequent intents 208 and class association rules 210 may be used to train an ML model 212, as discussed above. The set of frequent intents 208 may correspond to a set of labels used to label the training data 204. For example, in an embodiment, an unsupervised machine learning technique may be used to cluster or otherwise group the individual messages of the training data set into one or more categorical labels, such that each of the individual messages is associated with one or more of the categorical label(s). In some embodiments, the labels may be manually defined by a human author. In one embodiment, for example, thirteen frequent intents are identified, wherein each of the thirteen intents is associated with a description, and also with a rule set to execute when a message of the respective intent is received:

| Intent | Description | Example | Rule |
| --- | --- | --- | --- |
| 1. RefillRequest | The user wants a to refill the medication the pharmacy system notified her about | "Yes, please refill my medication" or "Yes, please" | Initiate a refill for the user. |
| 2. DontRefill | The user does not want to receive any refills for the medication being alerted, | "NO! Don't Refill" or "I don't want it" or "Please don't fill that prescription." | Do not refill any of the patient's prescriptions. Reply with a message letting her know that the pharmacy won't refill anything for her. |

-continued

| Intent | Description | Example | Rule |
|---|---|---|---|
| 3. CancelOrder | The user wants to cancel a previously placed Refill Reminder order. | "Please cancel that order" or "Oops, I actually don't need that anymore." | Cancel an order already in progress for that refill reminder, optionally considering the confidence factor produced by the trained ML model. |
| 4. DrivingInCar | The user is driving. | These messages often start with "I'm driving . . ." and may contain other custom messages that the user may edit for them. | Send a message letting the user know she can reply at a later point when she is in a safe place. Log the customer's/patient's identifier and driving time to avoid sending messages to that user at times when she is most likely in the car. |
| 5. OptInConfirm | The user wants to opt in to receiving further messages. | "Yes, I would love to receive messages" or "Send me messages" or "Sure, you can send me." | Opt the user's phone number in for text messages so that the pharmacy can send messages to that number in the future. |
| 6. OptOut | The user wants to opt out of receiving further messages. | "stop messaging me" or "stop sending" or "quit texting" | Opt that user and phone number out from future SMS messages. |
| 7. NeedsTimePickUp | The user wants to pick up her prescription later. | "I'll get it when I'm back from vacation" or "I'm going to pick it up, just hold on" or "I just need a few more days." | Extend the pick up window for that patient's ready-in-bin prescriptions in a pharmacy prescription filling system. |
| 8. StatusQuestion | The user wants the current status of her prescription. | "is it ready yet?" or "what's the current status" or "status please." | Perform a status and history lookup for the patient Respond in SMS with a status message to help provide status clarity for that patient. |
| 9. WrongNumber | The user is expressing that she received a message intended for someone else. | "wrong number" or "you have the wrong phone number" or "I don't know who this is." | De-link the patient with that particular phone number so that messages stop going out to that phone number. In an embodiment, use the confidence factor output by the trained ML model as a threshold. |
| 10. WrongPatient | The user is expressing that the wrong person in her household was messaged. | "you have the wrong person" or "this is Bill's phone number." | De-link the patient with that particular phone number so that messages stop going out to that phone number. In an embodiment, use the confidence factor output by the trained ML model as a threshold. |
| 11. ManualReview | The user needs assistance from a human. | "Please go ahead and also refill my Omnaprazole 20 mg please" and "The pharmacist told me that I should be switching to the generic version, so can you do that." | Automatically create customer service request support tickets for agents to review patient requests. Offer chat with pharmacy personnel as a means to help customers get immediate resolution for their requests. |

| Intent | Description | Example | Rule |
| --- | --- | --- | --- |
| 12. AlreadyPickedUp | The user has already picked up her prescription. | "I already picked that up" or "I have it already" or "I got it." | Record the event for tracking purposes Send the user a message apologizing and thanking them for their business. |
| 13. UnknownIntent | User intent cannot be determined, or cannot be determined with sufficient confidence (e.g., the patient was trying to reply to a spouse and accidentally used the wrong message thread, etc.). | "Hi Honey, can you pick up the kids on your way home from work?" or other unrelated personal matters | Reply to the patient with a message indicating that the pharmacy is not quite sure what patient wanted. In an embodiment, the pharmacy may manually review these messages from time to time to see if there are further classifications and decisioning logic that may be required to better handle these situations. |

The class association rules 210 may correspond to the rules in the above table. The rules may be encoded as program instructions that are executed with respect to a particular customer when messages of an associated type are received. Training the machine learning model 212 may include inputting labeled training data 204 and frequent intents 208 during training. The thirteen intents used to train the ML model, or any other suitable number and/or type of intents, may be stored in intents data 1206. It should be appreciated that the training data 204 may include only messages in list form and frequent intents 208 may include only labels/intents in list form. However, in some embodiments, training data 204 may be a hash map wherein the keys are unique messages and the values are non-unique intents selected from frequent intents 208, or references to non-unique intents in frequent intents 208.

Once the ML model 212 (or possibly multiple ML models) is trained, the ML model 212 may be operated. Input data 214, which may correspond to messages sent by the customer via the mobile device 102 in FIG. 1, may be input into the trained ML model 212. Input data 214 is generally message data (e.g., text messages) sent by customers, whether raw or pre-processed. Input data 214 may be input to the trained ML model 212 by the ML operation module 116 of FIG. 1, in one embodiment. The data flow diagram 200 may include producing results 216, when the trained ML model receives input data, wherein results 216 include an intent corresponding to the input data 214.

Example Machine Learning Model Code

Figure 3A:
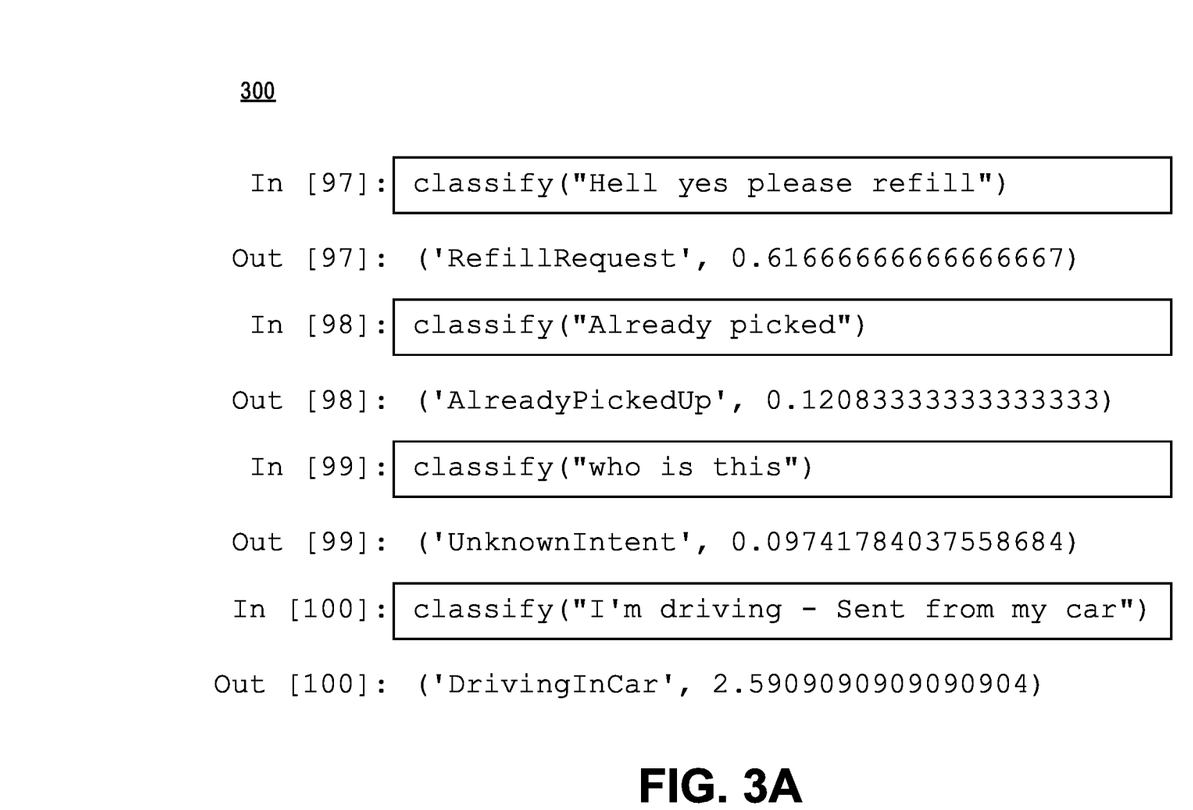
FIG. 3A is an example code listing for training, validating, and/or operating a machine learning model to facilitate a pharmacy customer order.

The methods and systems described herein may include numerous approaches to classification of customer messages. For example, FIG. 3A depicts an example listing 300 illustrating example inputs of a trained model (e.g., messages) and outputs of a trained model (e.g. intents and respective scores). The scores may include the Lancaster Stemming algorithm scoring, for example. Listing 300 includes applying stemming and scoring stop words, and training a model using labeled text message data, where the words of the data are converted to lowercase and stemmed. A corpus of words is created from the text message input. The model calculates a score relating any input message to an intent, such as one of the thirteen intents of FIG. 2. The score may represent a confidence that the text message is of that particular intent, for example. The intent having the highest score may be selected, which may indicate which of the intents is most strongly predicted by the application of the model to the text message. For example, at input line 98 of FIG. 3A, the text message reads "Already picked." The model is linked to a "classify" function, which when called using the text message as a parameter yields the output link 98 ('AlreadyPickedUp', 0,.12083333333333333). In this case, the model has correctly predicted an intent of AlreadyPickedUp, and provided a score of 0.12083333333333333.

Continuing the example, "Already picked." may be a text message that is typed into the mobile device 102 of FIG. 1. The mobile device 102 may transmit the text message, via the carrier mobile network 104, to the inbound module 106A of the external gateway 106. Assuming the external gateway 106 has sufficient memory, the inbound module 106A may optionally pass the message through the filter module 106C, to determine whether the message should be 1) discarded or 2) deferred (e.g., by storing the message to the message queue 106D for later processing and/or retrieval). Next, inbound module 106A may notify the internal gateway 108 that the text message is received. In some embodiments, the transfer of messages from the external gateway 106 may proceed by "push" (e.g., an HTTP POST message) messages being generated by the external gateway 106, or by "pull" (e.g., an HTTP GET message) messages being generated by the internal gateway 108. In either case, the message may be received/retrieved by the internal gateway 108. In the same fashion, internal gateway 108 may either push the message to the server 110, or the server 110 may pull the message. Once the message is received in the server 110, the message may be analyzed by the ML operation module 116 as discussed above. Continuing the example, the model operated by the ML operation module 116 may output an intent of AlreadyPickedUp, indicating the customer's position that she has already picked up this particular prescription from the pharmacy, and a confidence score of approximately 0.12.

The server 110 may then perform other actions. For example, the server 110 may perform an INSERT operation into the customer data 120C, which includes the customer's message, the date and time, and the output of the ML operation module 110. The server 110 may also send a reply message thanking the customer for the customer's message. The sending of reply messages by the server 110 may work in a manner similar to the receipt of messages, except that the POST and GET messages are reversed with respect to the internal gateway 108 and the external gateway 106, and the message transits through the outbound module 106B instead of the inbound module 106A.

Figure 3B:
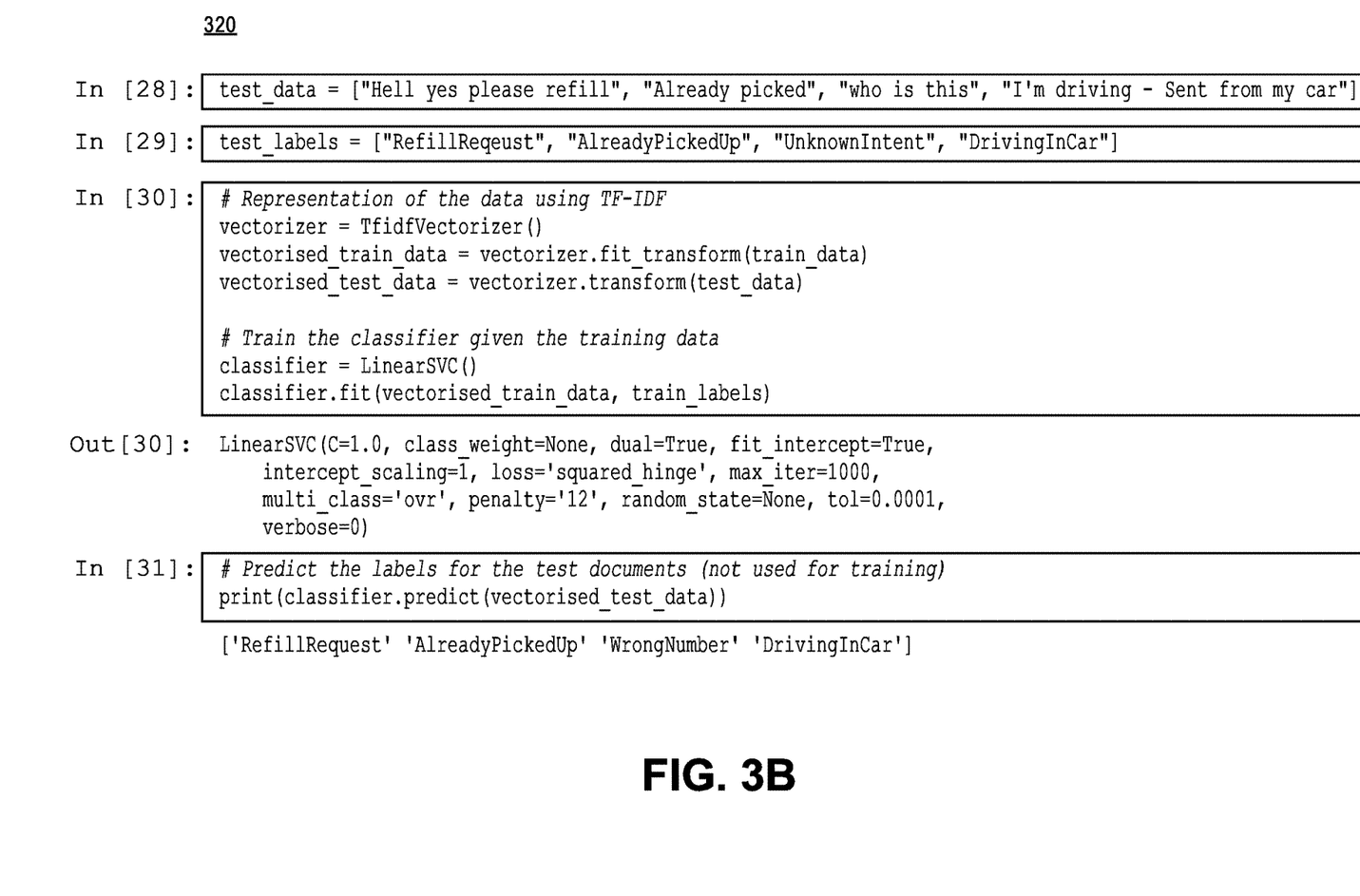
FIG. 3B is an example code listing for training, validating, and/or operating a machine learning model to facilitate a pharmacy customer order.

Turning now to FIG. 3B, another approach of training and operation of a machine learning model is depicted. FIG. 3B includes code listing 320, in which a list of customer text messages is input at line 28, and a list of respective intents is input at line 29. Each intent in the list of intents corresponds to one of the customer text messages in the list of customer text messages. The code listing 320 includes vectorizing the list of customer text messages and the list of intents using a Term Frequency-Inverse Document Frequency (TF-IDF) vectorizer, and using a linear support vector machine (SVM) to create a classifier model, using the two lists as labeled data. Finally, the code listing 320 includes using the trained classifier/model at line 31 to correctly predict labels with respect to test input messages, for verification purposes.

Figure 3C:
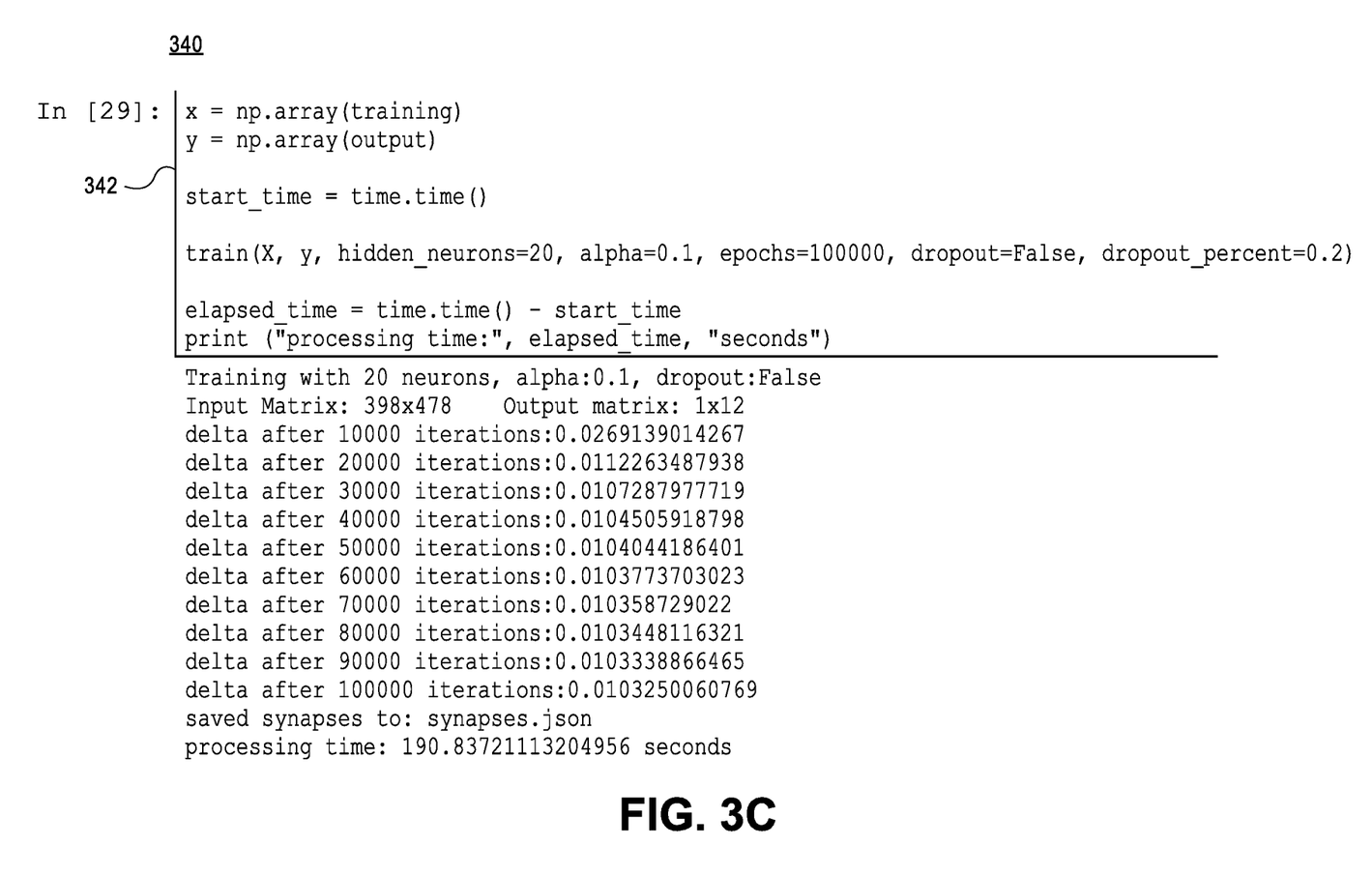
FIG. 3C is an example code listing for training, validating, and/or operating a machine learning model to facilitate a pharmacy customer order.
Figure 3D:
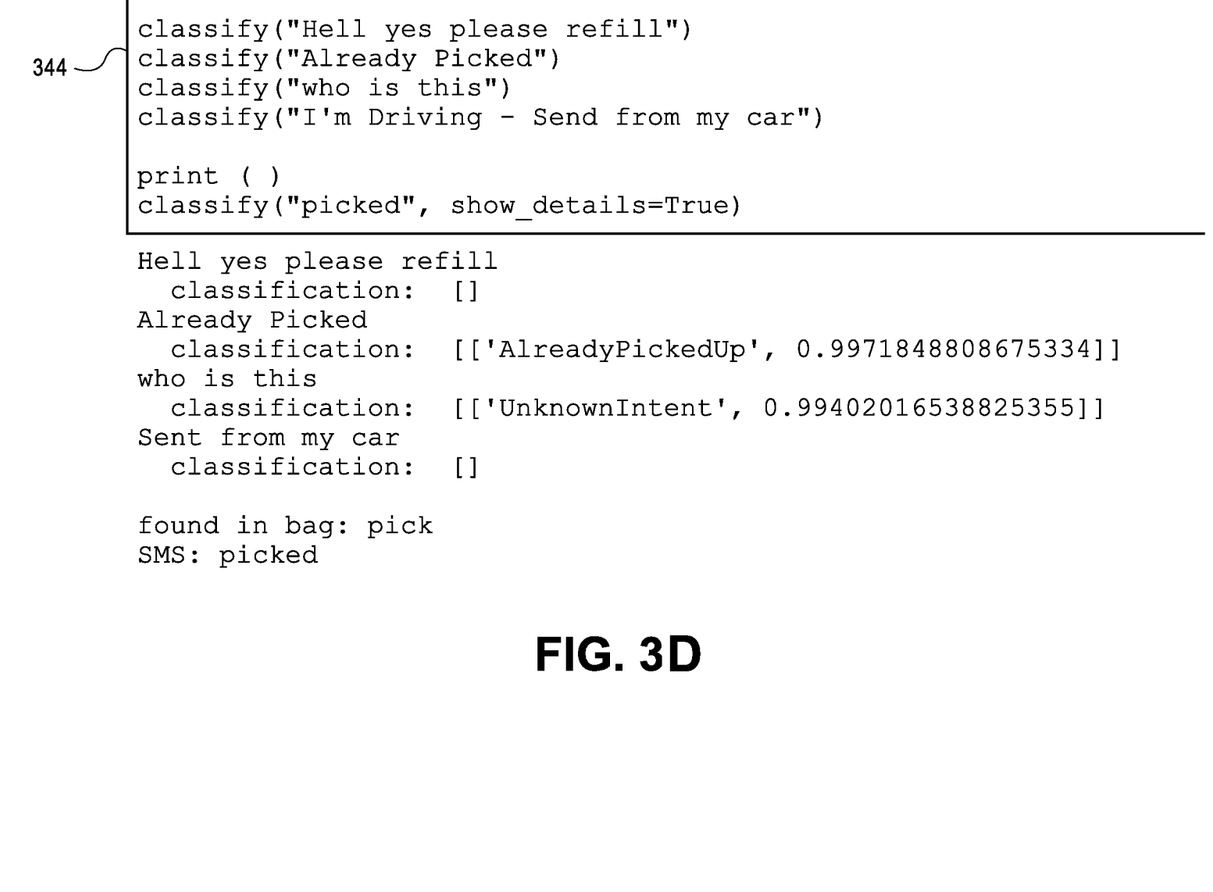
FIG. 3D is an example code listing for training, validating and/or operating a machine learning model to facilitate a pharmacy customer order.

FIG. 3C depicts yet another approach of training and operating a machine learning model. The code listing 340 includes an input 342 wherein a training input data set and a training output data set are passed as parameters to a train function, the train function having, in this example, 20 hidden neurons. The code listing 340 includes an output of training which demonstrates the error of the network becoming smaller and smaller, until a sufficiently large number of training iterations are made, such that the error is within an acceptable lower bound. Finally, the weights of the trained network are saved to a file. In an embodiment, the network weights may be saved to an electronic database, such as the training data 120A of FIG. 1. Training the artificial neural network in FIG. 3C may include labeling text messages of the customer, and tokenizing the words in the messages. The training may include stemming and converting the words in the messages into lowercase. The training may further include removing duplicates, and creating a bag of words. An activation function may be added to the end of the neural network which computes sigmoid non-linearity of the network to determine an output of the network. The artificial neural network may be trained using feed forward propagation, and a threshold may be applied. The text messages may be classified with a score. FIG. 3D depicts an example of using the trained neural network created in FIG. 3C to output an intent and a score, by applying a test text message of a customer to the artificial neural network.

Example Pharmacy Order Facilitation Methods

Figure 4:
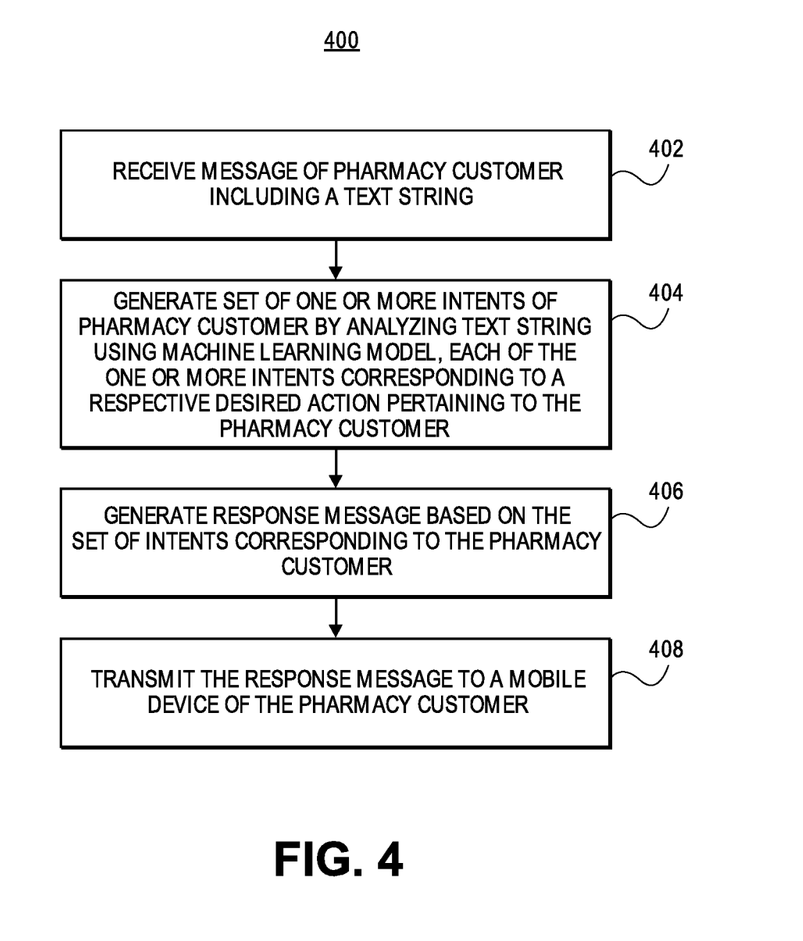
FIG. 4 is a flow diagram illustrating an exemplary method of facilitating a pharmacy order.

FIG. 4 is a flow diagram illustrating an exemplary method 400 of facilitating a pharmacy order. The method 400 may be implemented by the CPU 110A of server 100, for example, when executing instructions stored in the memory 110B. The method 400 may include receiving a message of a pharmacy customer including a text string (block 402). For example, the text string may be a text/SMS message such as the message "Already picked" in FIG. 3B. The text string may be generated by a user of the mobile device 102, and transmitted to the server 110 via the carrier network 104 as discussed above. As discussed above, the mobile device 102 may also be used, in some embodiments, to capture an audio recording of a pharmacy customer, which may be an utterance of that pharmacy customer. Such utterances may be recognized and/or converted to a text message. For example, the server 110 may include a voice-to-text module (not depicted in FIG. 1) that converts utterances to text messages.

Alternatively, the mobile device 102 may include a voice-to-text module (not depicted in FIG. 1) that converts utterances to text messages. The message may be received by the ML operation module 116, for instance.

Continuing with the above example, the ML operation module 116 may receive the message "Already picked" and may then input the message into a trained model, such as the classifier trained in FIG. 3B. Next, the classifier may generate a set of one or more intents of the pharmacy customer by analyzing the message (block 404), wherein each of the one or more intents in the set of one or more intents corresponds to a respective desired action of the pharmacy customer. The method 400 may also include generating a response message based on the intent(s) corresponding to the pharmacy customer (block 406). Continuing with the example, as discussed above with respect to FIG. 2 and FIG. 3A, the method 400 may generate a response that apologizes to the customer, and thanks the customer for his or her business. The method 400 may include transmitting the response message to a mobile device of the pharmacy customer (block 408), such as the mobile device 102.

In some embodiments, receiving the message of a pharmacy customer at block 402 may occur after the pharmacy has sent a message to a customer. For example, the "Already picked" message discussed above may be received by the pharmacy after the pharmacy has sent a message to the user regarding the status of a pharmacy order. The method 400 may include an additional block (not shown in FIG. 4) in which information about the customer is queried/obtained prior to transmitting the response to the customer at block 408. For example, information pertaining to the customer may be retrieved from the customer data 120C of FIG. 1.

In an embodiment, the text string received from the customer at block 402 may be one that was sent by a device of the customer without the customer's direct action. For example, the customer may be driving and may receive a notice from the pharmacy. If a "Driving InCar" intent is available, for instance, and a responsive text message from the customer's device is classified as corresponding to the Driving InCar intent (e.g., by reference to the signature block of the text message, or a "magic" string included in the text message), a response message to the pharmacy customer may be deferred or delayed. For example, block 408 may include tagging the response message with a deferral timeout or delay timeout. The response message may then be held until after the expiration of the timeout.

The method 400 may include an additional block (not shown in FIG. 4) in which a patient identifier (ID) of the customer is logged, along with the current time. Over time, the times at which a particular customer is driving may be learned (e.g., by server 110), and messages to the customer may be avoided at or proximate to those times. In general, each intent discussed with respect to FIG. 2, and/or other suitable intents, may be associated with a rule or instruction set, which may include looking up customer information from databases, and checking for state variables (e.g., timestamps, dates of last contact, etc.) to determine what next steps to take, if any. The table discussed with respect to FIG. 2 includes several examples of actions that may be taken when messages are determined to correspond to particular intents. For example, if the ML model determines with high confidence that a message corresponds to a RefillRequest, then information (e.g., the patient ID) may be transmitted to a computer system and/or an software module. For example, the patient ID may be sent to a refill module, which identifies any pending refill inquiries matching the patient ID. The refill module may initiate a refill if a match is found.

For example, on January 1, a prescription refill system may send a refill reminder outbound message to a pharmacy customer via SMS. The message may read, "It looks like your budesonide inhaler, 90 mcg/actuation is due for refill. Do you wish to refill your prescription?" The prescription refill system may operate as a batch process, and may create a database record, linked to the customer in customer data 120C by patient ID, when the outbound message is sent. On January 3, the customer may reply with an inbound message stating that, "Hello, yes I would like to refill that." After analysis by the ML model determines that the message is of type RefillRequest, the ML operation module 116 of FIG. 1 may transmit a message such as "(RefillRequest: Yes, PatientID: XYZ123)" to the prescription refill system, wherein the patient ID is associated with the customer. The prescription refill system may receive the message and may look for a database record based on the patient ID. The database record may include an indication of the medication, the delivery mechanism, and the dosage. Other information may be included, such as the status as a controlled substance, precautions, etc.

Once the prescription refill system locates the record of the patient based on the patient ID, the prescription refill system may take additional actions, such as causing a prescription fill order to be transmitted to a default local pharmacy of the customer, or a prescription mailing service to generate a postal mail order to the customer, where the refill is included in the mailing.

ADDITIONAL CONSIDERATIONS

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for implementing the concepts disclosed herein, through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A computer-implemented method of facilitating a pharmacy order, comprising:
   receiving, in an application server, a message of a pharmacy customer, the message including a text string;
   training a machine learning model using training data including a set of messages each having a respective intent label specifying an objective of a pharmacy customer;
   generating, by analyzing the text string using the trained machine learning model, a set of one or more intents of the pharmacy customer, each of the one or more intents corresponding to a respective desired action pertaining to the pharmacy order;
   generating, based on the set of intents corresponding to the pharmacy customer, at least one response message; and
   transmitting the at least one response message to a mobile device associated with the pharmacy customer.

2. The computer-implemented method of claim 1, wherein receiving the message of the pharmacy customer includes receiving a text message via a mobile telephone carrier.

3. The computer-implemented method of claim 1, wherein analyzing the text string using the trained machine learning model includes analyzing the text string using a classifier model.

4. The computer-implemented method of claim 1, wherein generating the at least one response message includes generating a confirmation based on an intent of the customer.

5. The computer-implemented method of claim 1, wherein generating the at least one response message includes generating a message deferral timeout.

6. The computer-implemented method of claim 5, wherein transmitting the at least one response message to the mobile device associated with the pharmacy customer includes delaying the transmission of the at least one response message until the message deferral timeout has elapsed.

7. The computer-implemented method of claim 5, wherein generating the message deferral timeout is based on the set of intents corresponding to the pharmacy customer including an intent indicating that the pharmacy customer is driving.

8. The computer-implemented method of claim 1, wherein transmitting the at least one response message to the mobile device associated with the pharmacy customer includes transmitting a text message to the mobile device.

9. The computer-implemented method of claim 1, wherein:
generating the set of one or more intents includes generating an intent corresponding to a prescription refill request;
generating the at least one response message includes generating a refill confirmation message based on the intent corresponding to a prescription refill request; and
transmitting the at least one response message to the mobile device associated with the pharmacy customer includes transmitting the refill confirmation message to the mobile device.

10. A computing system comprising:
one or more processors; and
memory storing instructions that, when executed by the one or more processors, cause the computing system to:
receive, in an application server, a message of a pharmacy customer, the message including a text string;
train a machine learning model using training data including a set of messages each having a respective intent label specifying an objective of a pharmacy customer;
select, from a set of one or more trained machine learning models, the trained machine learning model;
generate, by analyzing the text string using the trained machine learning model, a set of one or more intents of the pharmacy customer, each of the one or more intents corresponding to a respective desired action pertaining to the pharmacy order;
generate, based on the set of intents corresponding to the pharmacy customer, at least one response message;
transmit the at least one response message to a mobile device associated with the pharmacy customer; and
cause the at least one response message to be displayed in a display device of the mobile device.

11. The computing system of claim 10, wherein the memory stores further instructions that, when executed by the one or more processors, cause the computing system to:
receive a text message via a mobile telephone carrier.

12. The computing system of claim 10, wherein the memory stores further instructions that, when executed by the one or more processors, cause the computing system to:
analyze the text string using a classifier model.

13. The computing system of claim 10, wherein the memory stores further instructions that, when executed by the one or more processors, cause the computing system to:
generate a confirmation based on an intent of the customer.

14. The computing system of claim 10, wherein the memory stores further instructions that, when executed by the one or more processors, cause the computing system to:
generate a message deferral timeout.

15. The computing system of claim 10, wherein the memory stores further instructions that, when executed by the one or more processors, cause the computing system to:
transmit a text message to the mobile device.

16. The computing system of claim 14, wherein the memory stores further instructions that, when executed by the one or more processors, cause the computing system to:
delay and/or defer the transmission of the at least one response message until the message deferral timeout has elapsed.

17. The computing system of claim 10, wherein the memory stores further instructions that, when executed by the one or more processors, cause the computing system to:
initiate a pharmacy prescription refill of a prescription associated with the pharmacy customer based on the set of intents corresponding to the pharmacy customer.

18. A computing system comprising:
a mobile device configured to execute an application that causes an inbound message to be transmitted via a carrier network;
a server device configured to execute an application that causes the inbound message to be received via the carrier network, wherein the server device is configured to, after receiving the inbound message via the carrier network;
train a machine learning model using training data including a set of messages each having a respective intent label specifying an objective of a pharmacy customer;
analyze the inbound message using the trained machine learning model;
identify a customer intent corresponding to the inbound message;
based on the customer intent, perform an action with respect to a pharmacy order corresponding to the customer;
generate an outbound text message addressed to the mobile device; and
transmit the outbound text message to the mobile device via the carrier network.

19. The computing system of claim 18, wherein the customer intent corresponding to the inbound message pertains to the status of a pharmacy order.

20. The computing system of claim 18, wherein the server device is configured to query an electronic database to look up information related to a customer based on metadata associated with the inbound message.

* * * * *